United States Patent [19]

Markham, Charles W.

[11] Patent Number: 4,705,050
[45] Date of Patent: Nov. 10, 1987

[54] MOISTURE-ACTIVATED FLOATATION DEVICE

[76] Inventor: Markham, Charles W., 667 Snug Island, Clearwater Beach, Fla. 33515

[21] Appl. No.: 783,157

[22] Filed: Oct. 2, 1985

[51] Int. Cl.⁴ ............................................. A01F 5/441
[52] U.S. Cl. .............................. 128/749; 604/385 A; 441/98
[58] Field of Search ............... 128/749, 756, 759, 760, 128/762, 767; 441/98; 604/385 R, 364, 366, 367, 375; 428/913, 304 A, 305.5; 521/56, 57, 77; 156/77, 78, 79

[56] References Cited

U.S. PATENT DOCUMENTS

| | | | |
|---|---|---|---|
| 3,812,001 | 5/1974 | Ryan | 604/385 R |
| 3,881,491 | 5/1975 | Whyte | 604/385 R |
| 4,163,822 | 8/1979 | Walter | 156/77 |
| 4,333,780 | 6/1982 | Allada | 156/78 |
| 4,451,310 | 5/1984 | Lairloup | 156/78 |

FOREIGN PATENT DOCUMENTS 1354198  1/1984  France .................................. 156/77

Primary Examiner—Stephen C. Pellegrino
Assistant Examiner—John D. Ferros
Attorney, Agent, or Firm—A. W. Fisher, III

[57] ABSTRACT

A moisture-activated floatation device. In a first embodiment, a compound that evolves a gaseous fluid when wet is confined between two layers of sheet material capable of supporting a predetermined amount of weight when wet. The sheet material is hydrophilic and is specifically configured and dimensioned to fit into a water-flushed toilet bowl so that when the device is introduced into the bowl the water therein will activate the compound. The sheet material, when wet, is substantially impervious to the evolved gas so that such gas remains within the confines thereof and serves to provide buoyancy thereto. Feces deposited on the device will not sink but will be supported by the device until collected for testing. In a second embodiment, a gas-evolving compound is applied to one side of a single sheet of sheet material.

5 Claims, 3 Drawing Figures

MOISTURE-ACTIVATED FLOATATION DEVICE

BACKGROUND OF THE INVENTION

1. Field of the Invention

This invention relates to devices that facilitate the collection of human feces for medical testing purposes, and more specifically relates to a device used in connection with water-flushed toilets.

2. Description of the Prior Art

A search of United States patents that was conducted prior to the filing of this disclosure indicated that the following patents have been awarded for advancing the state of the art to which this invention pertains:

| Patentee | U.S. Pat. No. | Year of Issue |
| --- | --- | --- |
| James | 3,400,409 | 1968 |
| Nociti | 3,471,871 | 1969 |
| Gleichart | 3,486,172 | 1969 |
| Nagel | 3,588,921 | 1971 |
| Roberts, Jr. | 3,775,777 | 1973 |

None of the devices disclosed in the above-identified patents contact toilet bowl water when in use. Accordingly, none of the above-listed patents disclose or suggest that feces could be collected by a device made bouyant upon coming into contact with the water in a water-operated flush toilet.

In most modern hospitals, feces is collected by a device that bears a physical resemblance to a top hat. The "hat" is simply inverted and mounted by suitable means within the toilet bowl so that it collects feces deposited thereinto. The person collecting the sample must then retrieve it from the hat and clean the hat so that it may be used again as the hat is not disposable.

SUMMARY OF THE INVENTION

The longstanding need for a more suitable method and means for collecting feces for diagnostic test purposes is now fulfilled in the form of a moisture-activated floatation device. The device is dropped into a toilet bowl so that it contacts the water therein. The device is constructed in part of water-absorbant material, but the material is sufficiently strong when wet to maintain its structural integrity.

In a first embodiment, two (2) layers of the water-absorbant material are used, and in a second embodiment, a single layer of such sheet material is used.

In the first embodiment, a first layer of a suitable material is disposed in overlying relation to and in registration with a second layer of the same material, and a compound that evolves a gaseous fluid when wet is positioned therebetween. The compound is distributed substantially evenly throughout a number of individual compartments that are defined by suitable means between the two (2) layers of the water-loving but gas impervious when wet material.

In the second embodiment, the compound is applied, when in a flowable state, to one (1) side of the sheet material and is allowed to dry. Upon depositing the sheet material into a toilet bowl, the water therein reacts with the compound to form a foam that provides buoyancy to the material sufficient to keep it afloat even when supporting a charge of feces.

In either embodiment, the compound evolves a gas upon contact with the toilet bowl water and the gas provides the buoyancy required to keep the sheet material afloat, even when burdened with the weight of fecal matter. This floatation of the sheet material maintains the feces against sinking so that samples thereon can be easily collected. The device, which is water soluble, can then be discarded by flushing the toilet.

The primary object of this invention is to provide a disposable device that supports feces deposited into a toilet bowl so that such feces does not sink under its own weight and render collection of samples thereof difficult and unsanitary.

Another object is to provide a feces-supporting platform that, when dry, can be stored in large quantities in a small space.

The invention accordingly comprises the features of construction, combination of elements and arrangement of parts that will be exemplified in the construction hereinafter set forth, and the scope of the ivention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
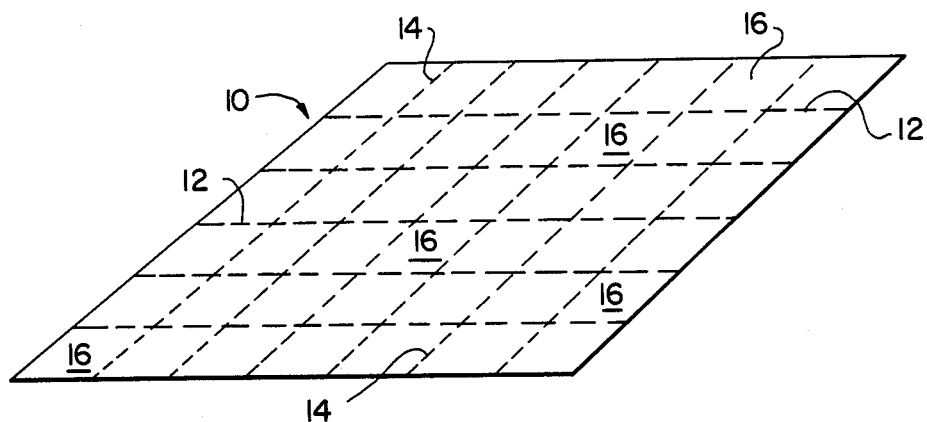
FIG. 1 is an isometric drawing of a first illustrative embodiment of the invention.

Refering now to FIG. 1, it will there be seen that the reference numeral 10 denotes a first embodiment of the invention as a whole. The fecal floater 10 is depicted as having a square configuration when seen in plan view, but it can be of any predetermined two-dimensional configuration. Its dimensions are such that it can fit within a toilet bowl when dropped thereinto.

The floater 10 is thin and has a generally planar form. It is formed by two (2) distinct layers of hydrophilic but gaseous fluid impervious when wet material such as the tissue paper manufactured under the trademark Protecto by a company of the same name. Other tissue-like papers are suitable as well, although toilet paper is not a suitable tissue as it loses its structural integrity when wet. The tissue must retain its strength when wet so as to support the feces deposited thereatop.

The row lines 12 and the column lines 14 appearing in FIG. 1 define a plurality of pockets or enclosed areas 16 between the two (2) layers of tissue paper when the invention is assembled. A water soluble adhesive is applied to the underlying layer of tissue paper in thin lines to define the rows and columns, preselected substantially equal amounts of the preferred gas-evolving when wet compound are distributed among the confines of each bounded region 16, and the overlying layer of tissue paper is placed atop the underlying layer. The adhesive secures the overlying layer of tissue paper to the underlying layer, along the row and column lines as aforesaid, thereby restricting each unit of compound within its enclosed area 16 as long as the floater 10 is kept dry. Adhesive is also applied to the perimeters of the layers as well so that compound units contiguous to such perimeters are also confined.

Many compounds are known that evolve a gaseous fluid when reacted with water, and all of such compounds are within the contemplation of this invention as indicated by the claims which follow this description. The preferred compound, due to its price and ready availability, is a mixture of citric acid and bicarbonate of soda.

When the floater 10 is dropped into a toilet bowl, the tissue paper will admit moisture through both the overlying and underlying layers of tissue paper into the compound-containing enclosed areas 16. The presence of moisture will initiate a gas-evolving chemical reaction. In view of the substantial impermeability of the tissue to gaseous fluid when such tissue is wet, the evolved gas, which is carbon dioxide when citric acid and bicarbonate of soda are employed as the compound, will be substantially retained within the confines of the enclosed areas 16.

Thus, the evolved gas will provide buoyancy to the floater 10 so that when feces is deposited thereatop, neither the floater 10 nor the feces will sink. This greatly facilitates the collection of specimens. Due to the water solubility of the adhesive, the floater 10 may be flushed away when the needed specimens have been collected.

Figure 2:
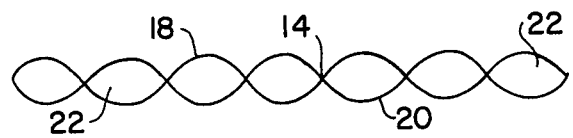
FIG. 2 is a transverse sectional view of the first embodiment of the invention when the compound has been activated by water.
Figure 3:
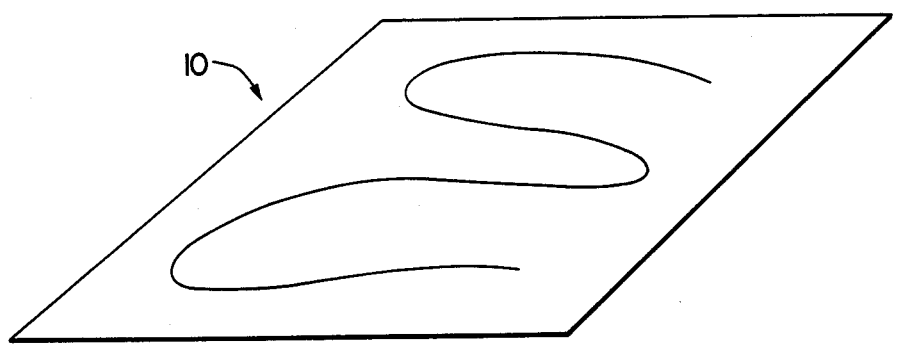
FIG. 3 is an isometric drawing of a second illustrative embodiment of the invention.

FIG. 2 is a sectional view showing overlying tissue layer 18 and underlying layer 20 after a gas has been evolved therebetween. The gas is denoted 22, it being understood that gas 22 is the result of the combination of water and the compound, which compound is not expressly illustrated.

In the second embodiment, a gas or foam-evolving when wet compound is applied to a single layer of tissue paper and allowed to dry. The sheet material is deposited into the toilet bowl so that the compound-containing side faces the water. The foam generated supports the substrate upon which the compound was applied and the invention is used in the same manner as its first embodiment. Many foam-evolving when wet compounds are known. For example, any foam-evolving polymer of suitable length is within the contemplation of this invention. Polyvinyl pyrrolidone is a typical suitable foaming agent. Moreover, shaving cream can be applied to a sheet of Protecto tissue paper or other suitable substrate and allowed to dry. Upon contact with water, it will foam and support the tissue in floating relation to the water and the buoyancy supplied by the foam will be sufficient to prevent the tissue and any feces thereatop from sinking.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A collection device to receive and support stool or feces for use with a toilet bowl to collect the stool or feces for medical testing; said collection device comprising a sheet of thin flexible material having a top and bottom side, said sheet of thin flexible material having a foam evolving compound adhered to said bottom side thereof such that when said collection device is placed within the toilet bowl, said foam evolving compound contacts the water within the toilet bowl forming a foam on said bottom side of said sheet of thin flexible material whereby said foam provides sufficient buoyancy to float said sheet of thin flexible material and the stool or feces thereon in floating relationship to the water within the toilet bowl to maintain the structural integrity of said sheet of thin flexible material and permit retrieval of the stool or feces supported on said top side of said sheet of thin flexible material for medical examination.

2. The collection device of claim 1 wherein said sheet of thin flexible material comprises tissue paper.

3. The collection device of claim 1 wherein said foam evolving compound comprises a foaming polymer of suitable length.

4. The collection device of claim 1 wherein said foam evolving compound comprises a polyvinyl pyrrolidone.

5. The collection device of claim 1 wherein said foam evolving compound comprises a dry shaving cream.

* * * * *